(12) United States Patent
Chou et al.

(10) Patent No.: US 6,943,893 B2
(45) Date of Patent: Sep. 13, 2005

(54) OPTICAL HETERODYNE SURFACE PLASMA WAVE DETECTING METHOD AND APPARATUS

(75) Inventors: Chen Chou, 5F, No. 37-3, Chuan-Yuan Rd., Pei-Tou Dist., Taipei City (TW); Wen-Chuan Kuo, Taipei (TW)

(73) Assignee: Chen Chou, Taipei (TW)

( * ) Notice: Subject to any disclaimer, the term of this patent is extended or adjusted under 35 U.S.C. 154(b) by 316 days.

(21) Appl. No.: 10/150,195

(22) Filed: May 17, 2002

(65) Prior Publication Data

US 2002/0180979 A1 Dec. 5, 2002

(30) Foreign Application Priority Data

May 21, 2001 (TW) ..................................... 90112140 A
Dec. 18, 2001 (TW) ..................................... 90131285 A

(51) Int. Cl.[7] .............................................. G01B 9/02
(52) U.S. Cl. ..................................................... 356/484
(58) Field of Search ................................. 356/484, 485, 356/486, 487, 491, 517, 450

(56) References Cited

U.S. PATENT DOCUMENTS

| | | | | |
|---|---|---|---|---|
| 5,585,921 A | * | 12/1996 | Pepper et al. | 356/487 |
| 5,847,468 A | * | 12/1998 | Nomura et al. | 257/797 |
| 5,978,074 A | * | 11/1999 | Opsal et al. | 356/72 |
| 6,157,199 A | * | 12/2000 | Park | 324/752 |
| 6,191,846 B1 | * | 2/2001 | Opsal et al. | 356/72 |
| 6,320,666 B1 | * | 11/2001 | Opsal et al. | 356/601 |

* cited by examiner

Primary Examiner—Samuel A. Turner
(74) Attorney, Agent, or Firm—Trop, Pruner & Hu, P.C.

(57) ABSTRACT

In an optical heterodyne surface plasma wave detecting method and apparatus, light that contains correlated $P_1$ and $P_2$ wave components (TM waves) is directed to a total reflective component such that two surface plasma waves are generated at an interface of a metal film and a test object. Light reflected from the total reflective component is detected to obtain an optical heterodyne test signal that is compared with an optical heterodyne reference signal to determine changes in at least one of amplitude and phase of the optical heterodyne signal relative to the optical heterodyne reference signal.

16 Claims, 13 Drawing Sheets

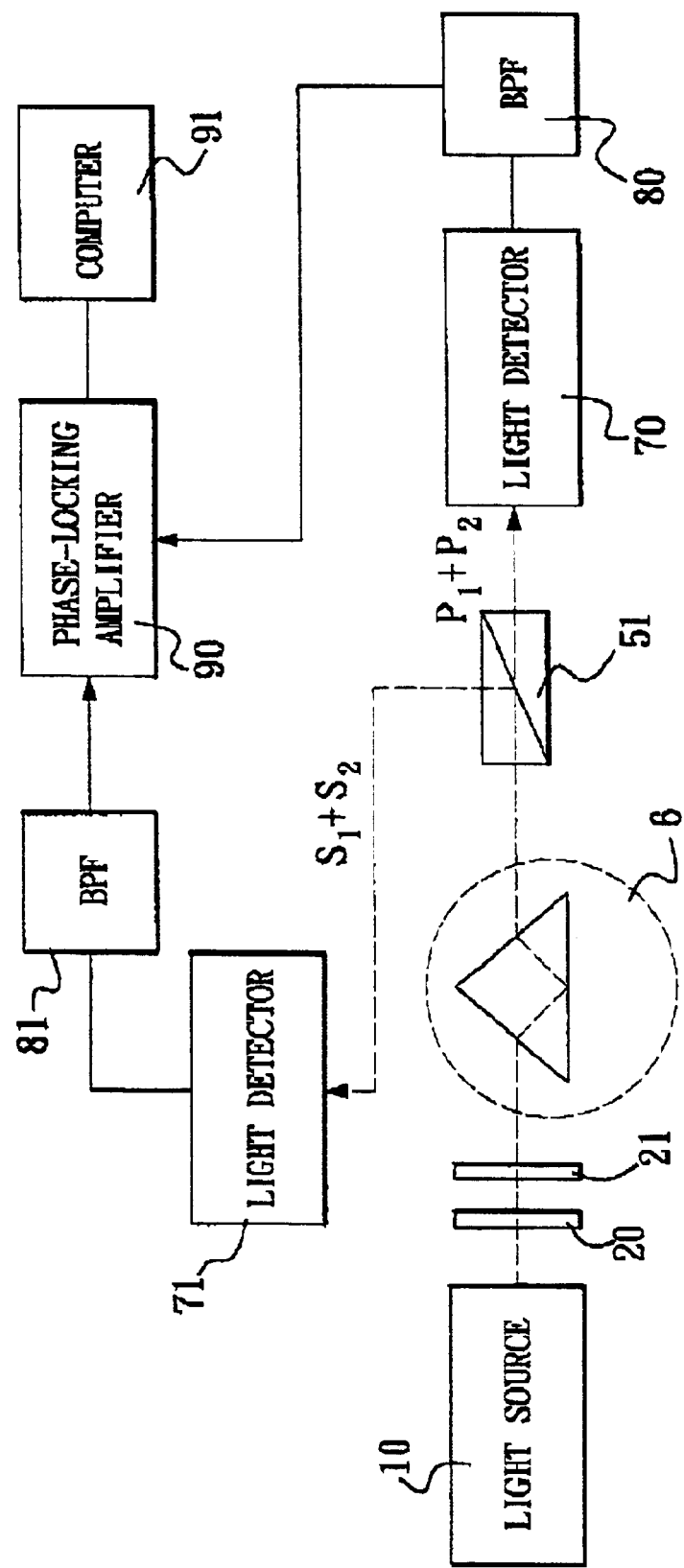
F I G. 13

OPTICAL HETERODYNE SURFACE PLASMA WAVE DETECTING METHOD AND APPARATUS

CROSS-REFERENCE TO RELATED APPLICATIONS

This application claims priority of Taiwanese Application No. 090112140, filed on May 21, 2001, and Taiwanese Application No. 090131285, filed on Dec. 18, 2001.

BACKGROUND OF THE INVENTION

1. Field of the Invention

The invention relates to a method and apparatus for detecting surface plasma waves, more particularly to an optical heterodyne surface plasma wave detecting method and apparatus.

2. Description of the Related Art

Conventional immunoassays, such as ELISA or RIA, for detecting pathogenic bacteria or virus require at least three days and involve repeated rinsing-reacting-rinsing operations. When optic fiber biosensors are in use, although the detection time can be shortened, they additionally require the aid of fluorescent markers.

A detecting method based on surface plasma resonance has been proposed heretofore to achieve fast detection without the need for fluorescent markers. As defined herein, surface plasma wave is an electromagnetic wave that oscillates at a metal surface. FIG. 1 illustrates how the phenomenon of surface plasma resonance can be realized. As shown, incident P-polarization light (TM wave) is directed by a total reflective component, such as a prism 60, to a metal film 61, thereby generating a surface plasma wave at an interface 610 between the metal film 61 and a test object on the interface 610 in a direction parallel to the interface 610. At the same time, energy of the incident P-polarization light is partly removed, thereby reducing the intensity of reflected light from the total reflective component.

By changing the incident angle ($\theta$), the wave vector ($k_x$) parallel to the interface 610 of the metal film 61 can approximate the wave vector ($k_{sp}$) of the surface plasma wave to satisfy the following resonance condition: $k_x = k_g \sin\theta = k_{sp}$, wherein $k_g = [\omega/c](\in_0)^{1/2}$, $k_{sp} = [\omega/c](\in_1\in_2/\in_1+\in_2)^{1/2}$, $\omega$ is the frequency of the incident light, and $\in_0$, $\in_1$, and $\in_2$ are the dielectric coefficients of the prism 60, the metal film 61 and the test object (not shown), As best shown in FIG. 2, a reduction in reflectivity becomes more and more evident when the resonance condition is satisfied.

With further reference to FIG. 3, a change in the dielectric coefficient ($\in_z$) or refractive index will lead to a shift in the resonance angle. By measuring this shift, a change in physical property, such as the refractive index, concentration, etc., can be observed. The change in physical property can be similarly observed by measuring a change in the intensity of the reflected light under fixed incident angle conditions. Accordingly, the time-varying change in physical property can be also monitored to result in the curve of FIG. 4.

The above detection methods are widely used in the fields of biomedicine and material chemistry. However, regardless of whether the change in the intensity of the reflected light or the change in the resonance angle is relied upon in the detection of physical properties, the aforesaid conventional detection methods are still unsatisfactory in view of their relatively low sensitivity.

SUMMARY OF THE INVENTION

Therefore, the main object of the present invention is to provide an optical heterodyne surface plasma wave detecting method and apparatus suitable for fast and real-time detections with high sensitivity.

According to one aspect of the invention, an optical heterodyne surface plasma wave detecting method is provided for measuring changes in dielectric coefficient or refractive index attributed to a test object on a known total reflective component, such as a prism. The total reflective component has an interface with the test object. The detecting method comprises the steps of:

(a) processing a coherent light beam from a two-frequency orthogonal linear or circular polarized coherent light source to form a reference light beam and a signal light beam, each of the reference light beam and the signal light beam having correlated $P_1$ and $P_2$ components (TM waves), the correlated $P_1$ and $P_2$ components having two different frequencies and parallel polarization directions;

b) directing the signal light beam to the total reflective component such that two surface plasma waves are generated at the interface;

c) detecting the reference light beam and light reflected from the total reflective component so as to obtain an optical heterodyne reference signal and an optical heterodyne test signal, respectively and d) comparing the optical heterodyne test signal with the optical heterodyne reference signal to determine changes in at least one of amplitude and phase of the optical heterodyne test signal relative to the optical heterodyne reference signal.

According to another aspect of the invention, an optical heterodyne surface plasma wave detecting method is provided for measuring changes in dielectric coefficient or refractive index attributed to a test object on a known total reflective component, such as a prism. The total reflective component has an interface with the test object. The detecting method comprises the steps of:

a) directing a coherent light beam from a two-frequency orthogonal linear or circular polarized coherent light source to the total reflective component such that two surface plasma waves are generated at the interface, the coherent light beam including a P-wave signal light beam (TM wave) and an S-wave reference light beam (TE wave), the P-wave signal light beam having correlated $P_1$ and $P_2$ components, the $P_1$ and $P_2$ components having two different frequencies and parallel polarization directions, the S-wave signal light beam having correlated $S_1$ and $S_2$ components, the $S_1$ and $S_2$ components having two different frequencies that are the same as those of the $P_1$ and $P_2$ components, respectively, the $S_1$ and $S_2$ components having parallel polarization directions that are orthogonal to those of the $P_1$ and $P_2$ components, b) splitting light reflected from the total reflective component into the reference light beam and the signal light beam via a polarized beam splitter;

c) detecting the reference light beam and the signal light beam so as to obtain an optical heterodyne reference signal and an optical heterodyne test signal, respectively, and d) comparing the optical heterodyne test signal with the optical heterodyne reference signal to determine changes in at least one of amplitude and phase of the optical heterodyne test signal relative to the optical heterodyne reference signal.

According to still another aspect of the invention, an optical heterodyne surface plasma wave detecting apparatus is provided for measuring changes in dielectric coefficient or refractive index attributed to a test object, and comprises:

a two-frequency orthogonal linear or circular polarized coherent light source for generating a reference light beam and a signal light beam, each of which has two correlated wave components, the wave components having two different frequencies and parallel polarization directions;

a total reflective component having an interface with the test object, the signal light beam being directed to the total reflective component such that two surface plasma waves are generated at the interface;

a first light detector for detecting the reference light beam so as to obtain an optical heterodyne reference signal;

a second light detector for detecting light reflected from the total reflective component 60 as to obtain an optical heterodyne test signal; and a signal processor, coupled to the first and second light detectors, for comparing the optical heterodyne test signal with the optical heterodyne reference signal to determine changes in at least one of amplitude and phase of the optical heterodyne test signal relative to the optical heterodyne reference signal.

According to yet another aspect of the invention, an optical heterodyne surface plasma wave detecting apparatus is provided for measuring changes in dielectric coefficient or refractive index attributed to a test object, and comprises:

a two-frequency orthogonal linear or circular polarized coherent light source for generating a P-wave signal light beam (TM wave) and an S-wave reference light beam (TE wave), the P-wave signal light beam having correlated $P_1$ and $P_2$ components, the $P_1$ and $P_2$ components having two different frequencies and parallel polarization directions, the S-wave signal light beam having correlated $S_1$ and $S_2$ components, the $S_1$ and $S_2$ components having two different frequencies that are the same as those of the $P_1$ and $P_2$ components, respectively, the $S_1$ and $S_2$ components having parallel polarization directions that are orthogonal to those of the $P_1$ and $P_2$ components;

a total reflective component having an interface with the test object, light from the coherent light source being directed to the total reflective component such that two surface plasma waves are generated at the interface;

a polarized beam splitter for splitting light reflected from the total reflective component into the reference light beam and the signal light beam;

a first light detector for detecting the reference light beam so as to obtain an optical heterodyne reference signal;

a second light detector for detecting the signal light beam so as to obtain an optical heterodyne test signal; and a signal processor, coupled to the first and second light detectors, for comparing the optical heterodyne test signal with the optical heterodyne reference signal to determine changes in at least one of amplitude and phase of the optical heterodyne signal relative to the optical heterodyne reference signal.

According to a further aspect of the invention, an optical heterodyne surface plasma wave detecting method is provided for measuring changes in dielectric coefficient or refractive index attributed to a test object on a known total reflective component, such as a prism. The total reflective component has an interface with the test object. The detecting method comprises the steps of:

a) generating a signal light beam having correlated $P_1$ and $P_2$ components (TM wave), the correlated $P_1$ and $P_2$ components having two different frequencies and parallel polarization directions;

b) directing the signal light beam to the total reflective component such that two surface plasma waves are generated at the interface;

c) detecting light which is reflected from the total reflective component so as to obtain an optical heterodyne test signal; and d) determining a time-varying change in amplitude of the optical heterodyne test signal.

According to still a further aspect of the invention, an optical heterodyne surface plasma wave detecting apparatus is provided for measuring changes in dielectric coefficient or refractive index attributed to a test object, and comprises:

a two-frequency coherent light source for generating a signal light beam having correlated $P_1$ and $P_2$ components (TM wave), the correlated $P_1$ and $P_2$ components having two different frequencies and parallel polarization directions;

a total reflective component having an interface with the test object, the signal light beam being directed to the total reflective component such that two surface plasma waves are generated at the interface;

a light detector for detecting light reflected from the total reflective component so as to obtain an optical heterodyne test signal; and a signal processor, such as an amplitude demodulator coupled to the light detector, for determining a time-varying change in amplitude of the optical heterodyne test signal.

BRIEF DESCRIPTION OF THE DRAWINGS

Other features and advantages of the present invention will become apparent in the following detailed description of the preferred embodiments with reference to the accompanying drawings, of which:

FIG. 13 is a schematic diagram illustrating the third preferred embodiment of an optical heterodyne surface plasma wave detecting apparatus according to the present invention;

DETAILED DESCRIPTION OF THE PREFERRED EMBODIMENTS

Figure 1:
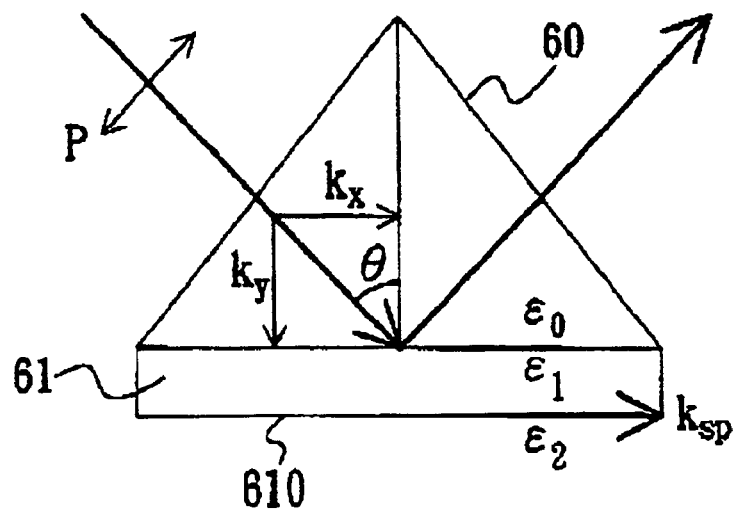
FIG. 1 illustrates a conventional mechanism for realizing surface plasma resonance.
Figure 2:
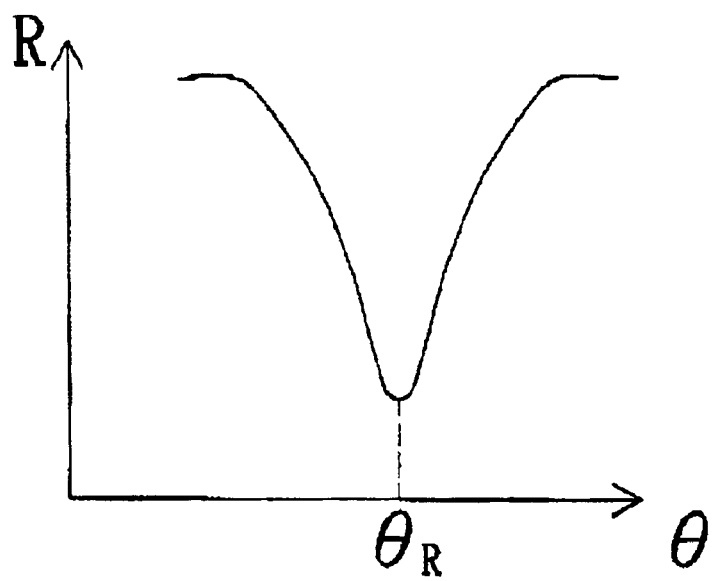
FIG. 2 is a plot illustrating how reflectivity varies with the incident angle in the conventional mechanism of FIG. 1.
Figure 3:
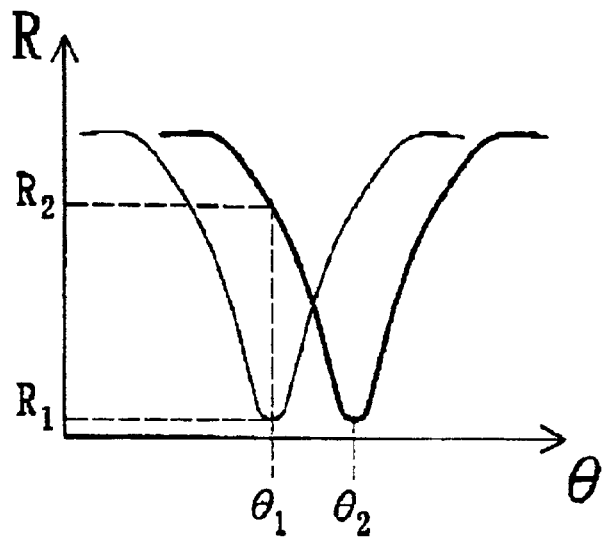
FIG. 3 is a plot illustrating how a change in a physical property of a test object varies the resonance angle in the conventional mechanism of FIG. 1.
Figure 4:
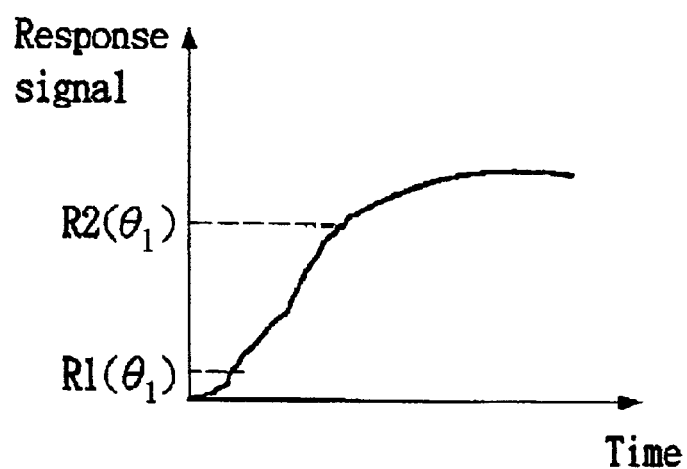
FIG. 4 is a plot illustrating how a time-varying change in the physical property of the test object can be monitored in the conventional mechanism of FIG. 1.

Before the present invention is described in greater detail, it should be noted that like elements are denoted by the same reference numerals throughout the disclosure.

In the present invention, instead of measuring the resonance angle or intensity of reflected light from a total reflective component, an optical heterodyne test signal reflected from the total reflective component is compared with an optical heterodyne reference signal to determine changes in at least one of amplitude and phase of the optical heterodyne test signal relative to the optical heterodyne reference signal. Aside from higher sensitivity, the detecting method and apparatus according to this invention were found to be suitable for real-time measurement of molecular interaction, such as kinetics of association, kinetics of disassociation, concentration, surface coverage, etc., and have potential for use as chemical sensors or biosensors.

Figure 5:
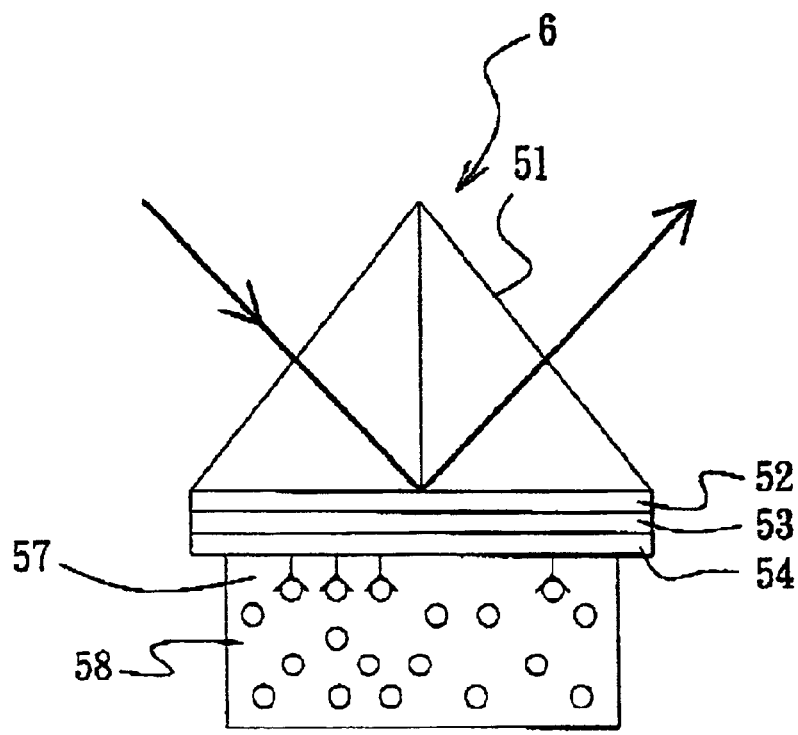
FIG. 5 illustrates a general total reflective component of the first preferred embodiment of an optical heterodyne surface plasma wave detecting apparatus of this invention when used as a biosensor.

FIG. 5 illustrates a general total reflective component 6 of the first preferred embodiment of an optical heterodyne surface plasma wave detecting apparatus according to this invention. The total reflective component 6 includes a prism 51 and a glass substrate 53 at a base of the prism 51. The glass substrate 53 has one side opposite to the base of the prism 51 and plated with a metal film, such as gold or silver, having a thickness of about 50 nm. Between the prism 51 and the glass substrate 53, a layer 52 of index matching oil is provided to ensure that the prism 51 and the glass substrate 53 have uniform refractive indices. The refractive index of the metal film is lower than those of the prism 51 and the glass substrate 53. A chemical film 54, e.g. self-assembly monolayer or SAM, is deposited on the surface of the metal film, and can interact with molecules in a reactor 58 having the same characteristics to form reaction products 57, such as antibody-antigen reaction products 57. Two surface plasma waves (spw1, spw2) will be affected by the reaction products 57 on the surface of the metal film to thereby vary the refractive index. As such, the amplitude of an optical heterodyne test signal formed from reflected and correlated $P_1$ and $P_2$ components (TM wave) can be varied accordingly. Thereafter, with the use of a phase-locking amplifier or an amplitude demodulator, at least one of the amplitude and phase of the optical heterodyne test signal can be measured in real-time for real-time detection of physical property changes, i.e. molecular interaction.

Figure 6:
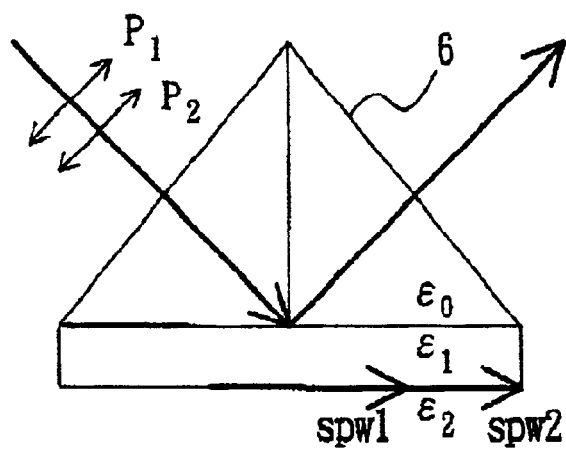
FIG. 6 illustrates how two surface plasma waves are generated in the total reflective component of FIG. 5.
Figure 7:
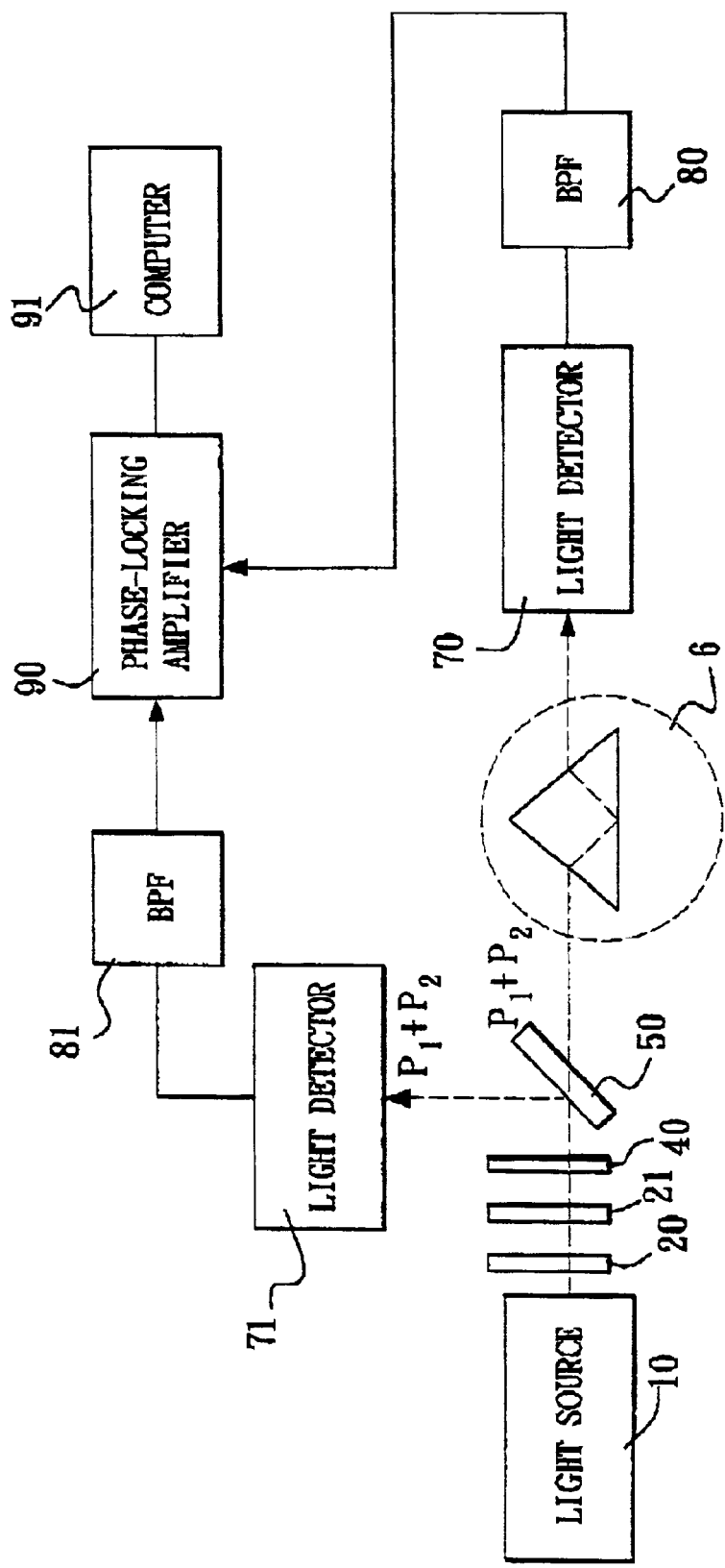
FIG. 7 is a schematic diagram illustrating the first preferred embodiment.

FIGS. 6 and 7 illustrate the first preferred embodiment of the optical heterodyne surface plasma wave detecting apparatus according to this invention. Light source 10 is a stabilized two-frequency laser, such as a Zeeman laser, capable of generating mutually orthogonal linear polarized light beams, i.e. P-wave (TM wave) and S-wave (TE wave), at two different frequencies. The P-wave light beam has an amplitude ($A_p$) and a frequency ($\omega_p$). The S-wave light beam has an amplitude ($A_s$) and a frequency ($\omega_s$). Light from the light source 10 passes through a $\lambda/2$ plate 20 for adjusting the azimuth angle such that the P-wave light beam is parallel to the X-axis and can be represented by $$A_p e^{i\omega_p t}\begin{bmatrix}1\\0\end{bmatrix},$$

and such that the S-wave light beam is parallel to the Y-axis and can be represented by $$A_s e^{i\omega_s t}\begin{bmatrix}0\\1\end{bmatrix}.$$

When the P-wave and S-wave light beams pass subsequently through a $\lambda/4$ plate 21 such that the azimuth angle is set to 45 relative to the x-axis, they will be converted into right-rotated (R-wave) and left-rotated (L-wave) circular polarized light beams, respectively, wherein $$R = (1/\sqrt{2})A_p e^{i\omega_p t}\begin{bmatrix}1\\-i\end{bmatrix} \text{ and } L = (1/\sqrt{2})A_s e^{i\omega_s t}\begin{bmatrix}1\\i\end{bmatrix}.$$

Thereafter, the R-wave and L-wave light beams are received by a polarizer 40, which allows the P-wave components of the R-wave and L-wave light beams to pass therethrough, thereby resulting in the $P_1$ wave component and the $P_2$ wave component having two different frequencies, wherein $$P_1 = (1/\sqrt{2})A_p\begin{bmatrix}1\\0\end{bmatrix}e^{i\omega_p t} \text{ and } P_2 = (1/\sqrt{2})A_s\begin{bmatrix}1\\0\end{bmatrix}e^{i\omega_s t}.$$

A beam splitter 50 then separates the light from the polarizer 40 into a signal light beam and a reference light beam.

The signal light beam is incident upon the total reflective component 6, which is rotatable so as to vary the incident angle. When the incident angle is equal or close to the surface plasma resonance angle, two surface plasma waves will be generated at the interface of the metal film and the test object and are attributed to the correlated $P_1$ and $P_2$ wave components having different frequencies. A light detector 70 receives the $P_1$ and $P_2$ wave components reflected from the total reflective component 6 to result in an optical heterodyne test signal having a beat frequency ($\Delta\omega$) equal to $\omega_p - \omega_s$. The optical heterodyne test signal can be represented by the following Equation (1):

$$I_{sig}(\Delta\omega t) = \tfrac{1}{2}(A_p')^2 + \tfrac{1}{2}(A_s')^2 + A_p' A_s' \cos(\Delta\omega t + \Delta\Phi') \qquad (1)$$

wherein $\Delta\Phi' = \Phi_{P1}' - \Phi_{P2}'$, $A_p'$ and $A_s'$ are the amplitudes of the reflected $P_1$ and $P_2$ wave components, and $\Phi_{P1}'$ and $\Phi_{P2}'$ are the phase angles of the reflected $P_1$ and $P_2$ wave components. The output of the light detector 70 is processed by a band pass filter (BPF) 80 having a center frequency equal to the beat frequency ($\Delta\omega$). The AC output of the band pass filter 80, which is provided to a signal processor, such as a phase-locking amplifier 90, is represented by the following Equation (2):

$$I_{sig}(\Delta\omega t) = A_p' A_s' \cos(\Delta\omega t + \Delta\Phi') \qquad (2)$$

On the other hand, the reference light beam from the beam splitter 50 is received by a light detector 71 to obtain an optical heterodyne reference signal. The optical heterodyne reference signal can be represented by the following Equation (3):

$$I_{ref}(\Delta\omega t)=\tfrac{1}{2}A_p{}^2+\tfrac{1}{2}A_s{}^2+A_pA_s\cos(\Delta\omega t+\Delta\Phi) \quad (3)$$

wherein $\Delta\Phi=\Phi_{P1}-\Phi_{P2}=0$, $A_p$ and $A_s$ are the amplitudes of the reference $P_1$ and $P_2$ wave components, and $\Phi_{P1}$ and $\Phi P_2$ are the phase angles of the reference $P_1$ and $P_2$ wave components. The output of the light detector 71 is processed by a band pass filter 81 having a center frequency equal to the beat frequency ($\Delta\omega$). The AC output of the band pass filter 81, which is also provided to the phase-locking amplifier 90, is represented by the following Equation (4):

$$I_{ref}(\Delta\omega t)=A_pA_s\cos(\Delta\omega t) \quad (4)$$

With reference to the optical heterodyne reference signal, the phase-locking amplifier 90 will detect and amplify the optical heterodyne test signal, thereby enhancing both sensitivity and signal-to-noise ratio. The output of the phase-locking amplifier 90 is received by a computer 91 for real-time detection of the amplitude ($A_p'A_s'$) of the optical heterodyne test signal and the time-varying change in the phase ($\Delta\Phi'$) of the optical heterodyne test signal, thereby enabling real-time detection of interaction between chemicals or bio-molecules and the biosensor.

It should be apparent to one skilled in the art that the total reflective component can be one that employs an optical grating for the generation of surface plasma waves. Moreover, the light source of the first preferred embodiment may be replaced with any of the following: a single-frequency linear polarized laser in combination with a phase modulator, a polarizer and a Mach-Zender interferometer; a single-frequency linear polarized laser in combination with an electro-optic modulator having a fixed driving frequency; a semiconductor laser in combination with a current-modulated power source and a polarizer to form a Mach-Zender interferometer; a single-frequency linear polarized semiconductor laser in combination with a polarization-maintaining single mode optical fiber and integrated optical component and a phase modulator to form a Mach-Zender interferometer so as to obtain two-frequency correlated $P_1$ polarized light and $P_2$ polarized light; and a single-frequency P-wave linear polarized laser in combination with a phase modulator to form a Michelson interferometer so as to obtain two-frequency correlated $P_1$ polarized light and the $P_2$ polarized light.

Figure 8:
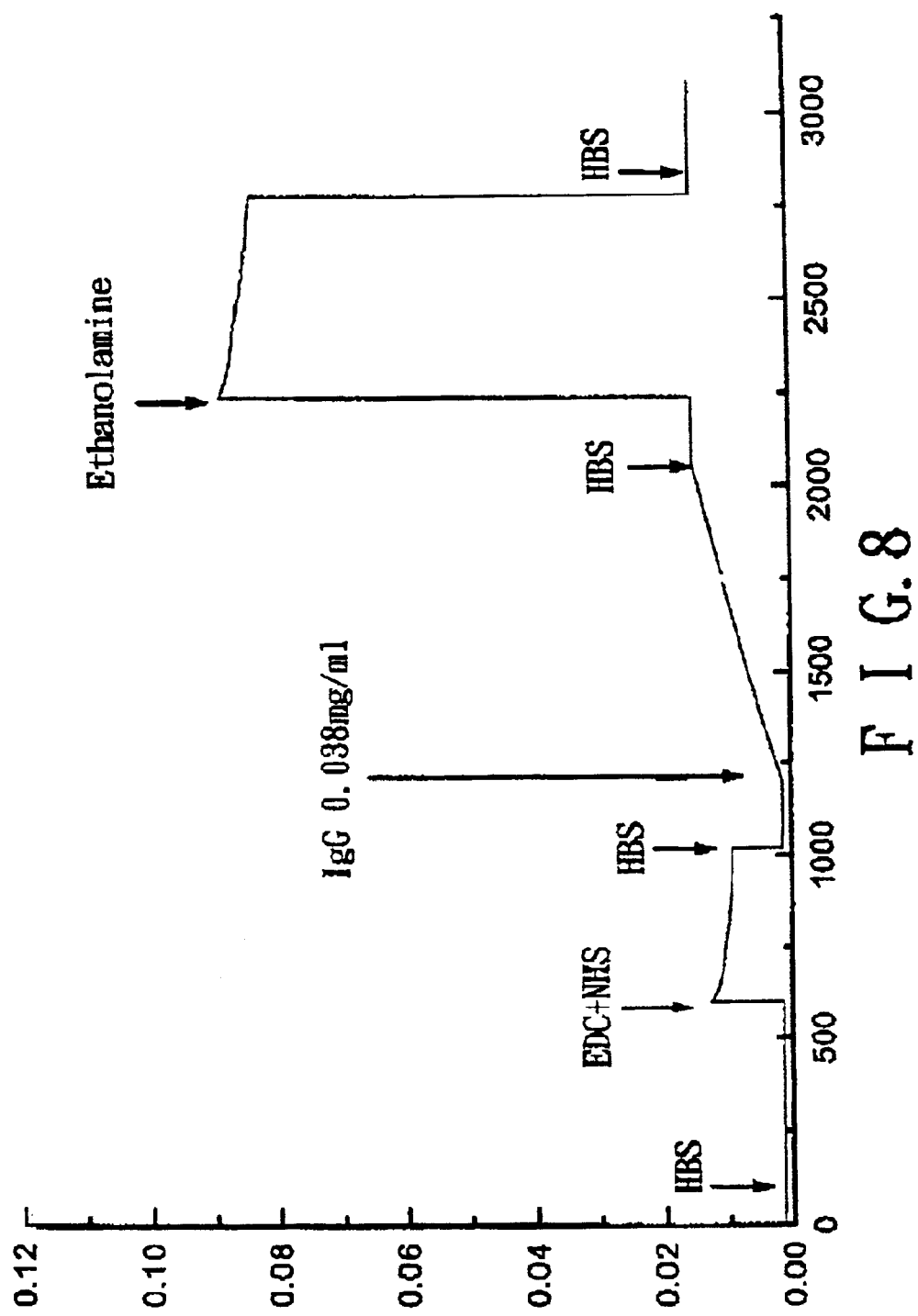
FIG. 8 illustrates a test result obtained according to the detecting apparatus of the first preferred embodiment when IgG antibodies (IgG concentration is 38 $\mu$g/ml) are fixed to the surface of the biosensor.
Figure 9:
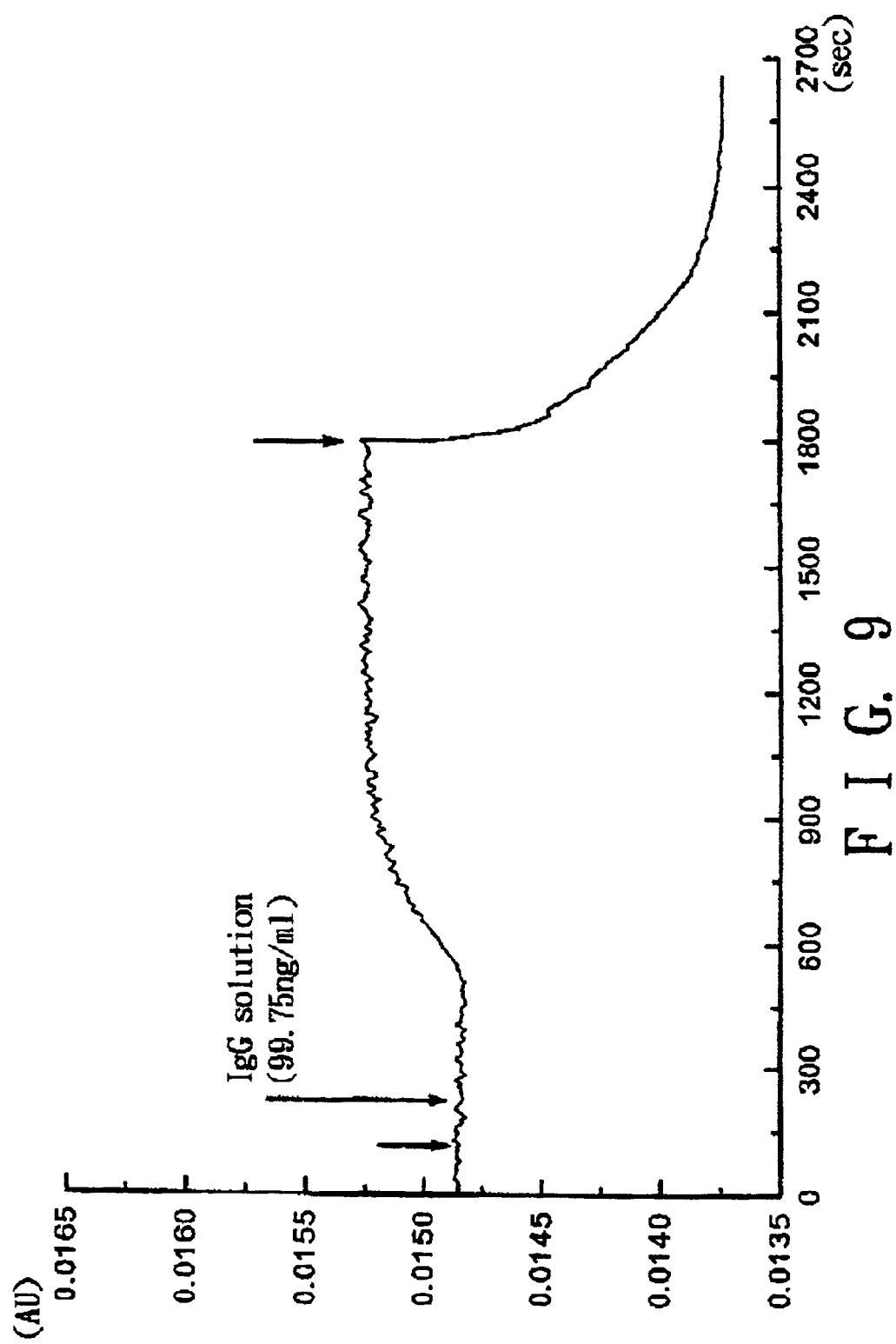
FIG. 9 illustrates a real-time reaction result obtained according to the detecting apparatus of the first preferred embodiment when IgG antibodies on the biosensor react with IgG antigen of a test sample.
Figure 10:
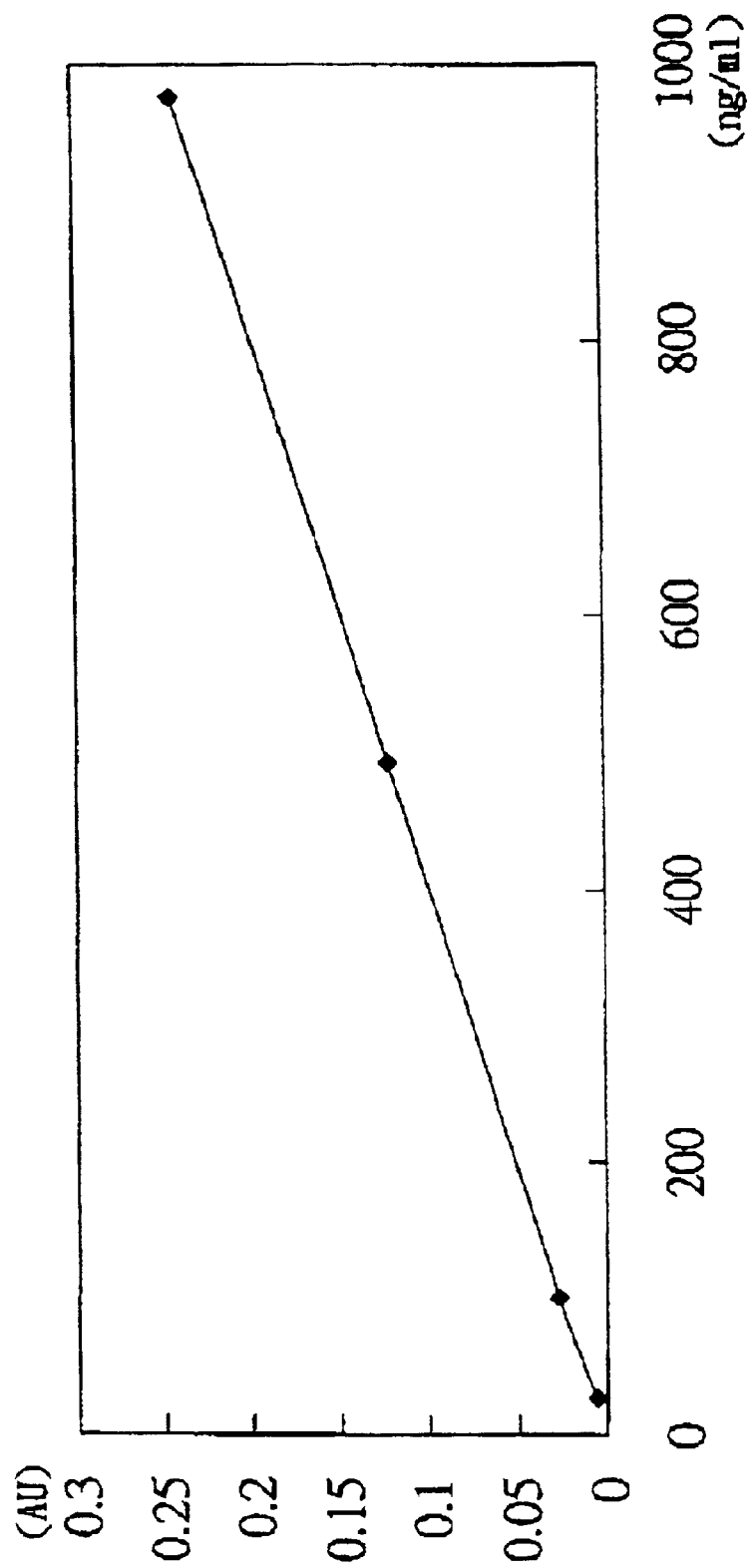
FIGS. 10 and 11 illustrate the dynamic range of detection of a detecting apparatus according to the first preferred embodiment in linear scale (ng/ml) and logarithmic scale (nM), respectively.
Figure 11:
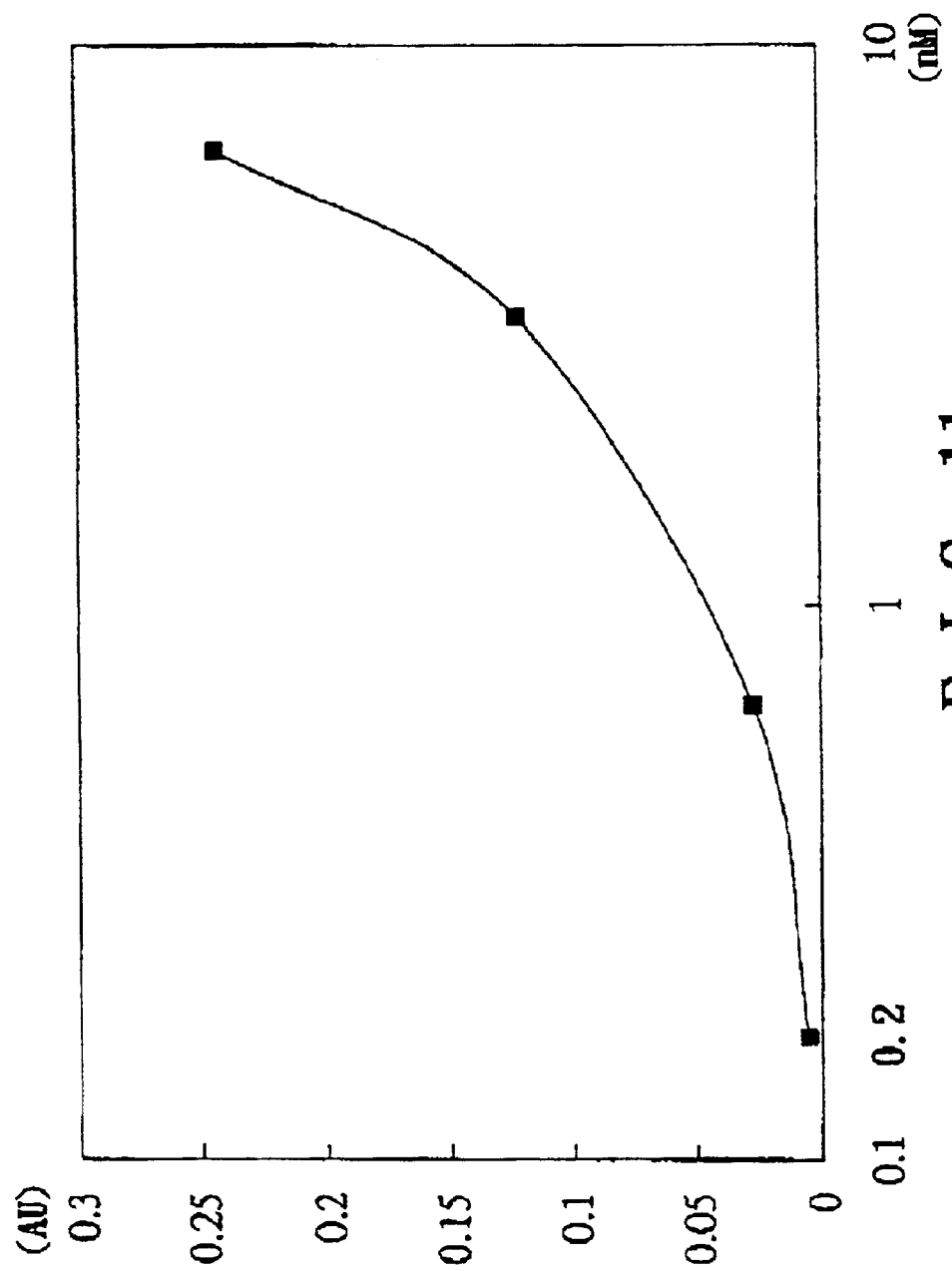

FIG. 8 illustrates a test result obtained according to the optical heterodyne surface plasma wave detecting apparatus of the first preferred embodiment when IgG antibodies are fixed to the surface of a biochip (BIAcore, CM5 chip). FIG. 9 illustrates a real-time reaction result obtained according to the optical heterodyne surface plasma wave detecting apparatus of the first preferred embodiment when IgG antibodies on the biochip react with IgG antigen (about 100 ng/ml) of a test sample. FIGS. 10 and 11 illustrate the dynamic range of detection of a detecting apparatus according to the first preferred embodiment in linear scale (ng/ml) and logarithmic scale (nM), respectively, for varying concentrations (25 ng/ml to 975.6 ng/ml or 0.2 nM to 8 nM) of a test object. It is apparent from these results that the sensitivity and the linear measurement range achievable in the present invention are up to 50 times more as compared to the conventional detection methods described beforehand.

Figure 12:
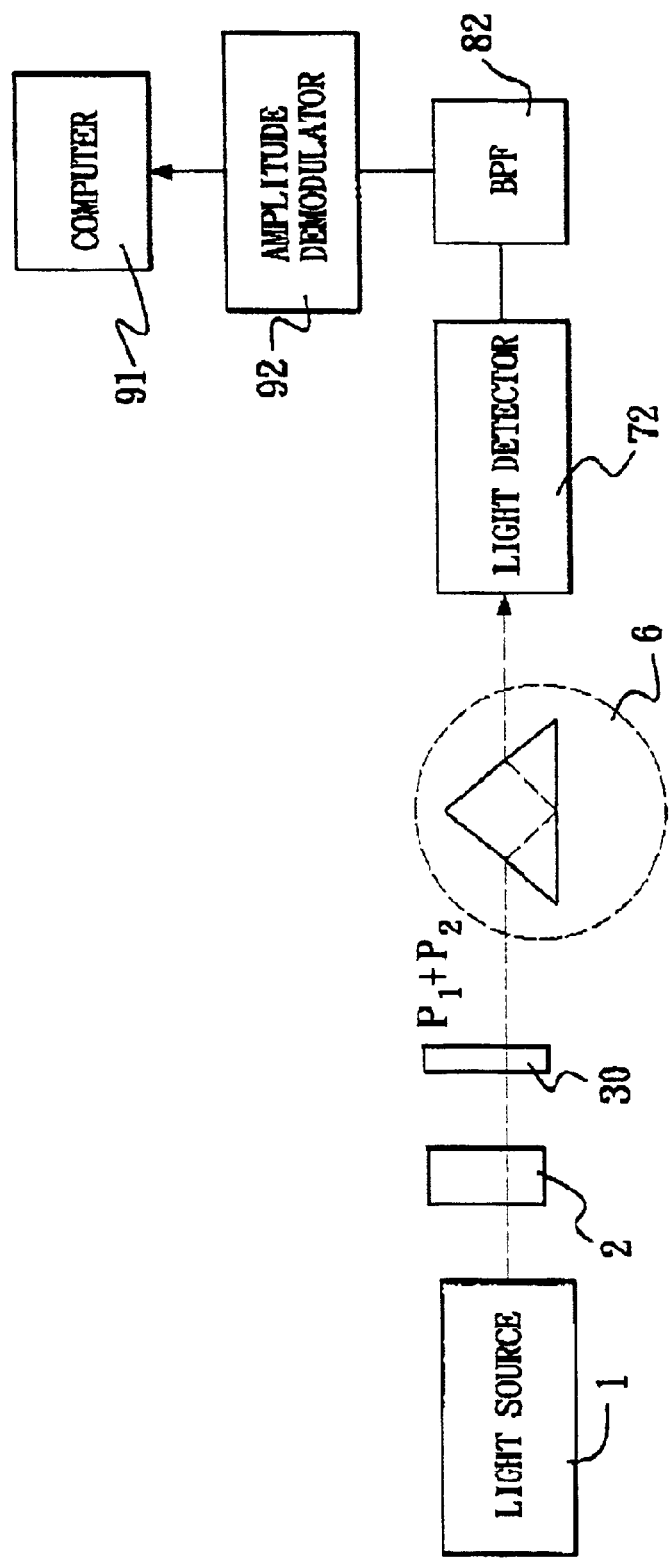
FIG. 12 is a schematic diagram illustrating the second preferred embodiment of an optical heterodyne surface plasma wave detecting apparatus according to the present invention.

The present invention further contemplates the use of an amplitude modulator, such as a digital voltmeter, to measure the amplitude of the optical heterodyne test signal. As shown in FIG. 12, the second preferred embodiment of an optical heterodyne surface plasma wave detecting apparatus according to this invention is transformed into a multi-channel detecting system. Light from a two-frequency orthogonal linear polarized laser light source 1 passes through a polarizer 2 to form two-frequency correlated $P_1$ wave and $P_2$ wave components. Upon passing through a cylindrical lens 30, the wave front is expanded to form a one-dimensional collimated beam that is incident upon the total reflective component 6. A one-dimension light detector 72, such as a CCD, receives light reflected from the total reflective component 6. The output of the light detector 72 is processed in sequence by a band pass filter 82 and an amplitude demodulator 92. A computer 91 receives the output of the amplitude demodulator 92 to achieve the multi-channel detecting function.

FIG. 13 illustrates the third preferred embodiment of an optical heterodyne surface plasma wave detecting apparatus according to this invention. Like the first preferred embodiment, light from a two-frequency orthogonal linear polarized coherent light source 10 passes through a $\lambda/2$ plate 20 and a $\lambda/4$ plate 21 to generate right-rotated (R-wave) and left-rotated (L-wave) circular polarized light. The R-wave and L-wave light are then directed to a total reflective component 6. The two-frequency $P_1$ wave and $P_2$ wave components of the R-wave and L-wave light can be represented by $$(1/\sqrt{2})A_p\begin{bmatrix}1\\0\end{bmatrix}e^{i\omega_p t} \text{ and } (1/\sqrt{2})A_s\begin{bmatrix}1\\0\end{bmatrix}e^{i\omega_s t},$$

whereas the two-frequency $S_1$ wave and $S_2$ wave components of the R-wave and L-wave light can be represented by $$-i(1/\sqrt{2})A_p\begin{bmatrix}0\\1\end{bmatrix}e^{i\omega_p t} \text{ and } i(1/\sqrt{2})A_s\begin{bmatrix}0\\1\end{bmatrix}e^{i\omega_s t}.$$

The total reflective component 6 is rotatable so as to vary the incident angle. When the incident angle is equal or close to the surface plasma resonance angle, two surface plasma waves will be generated at the interface of the metal film and the test object and are attributed to the correlated $P_1$ and $P_2$ wave components having different frequencies. A polarized beam splitter 51 separates light reflected from the total reflective component 6 into a signal light beam and a reference light beam. The signal light beam, which contains the reflected $P_1$ and $P_2$ wave components, is received by a light detector 70 to result in an optical heterodyne test signal having a beat frequency ($\Delta\omega$) equal to $\omega_p-\omega_s$. The optical heterodyne test signal can be represented by the following Equation (5):

$$I_{sig}(\Delta\omega t)=\tfrac{1}{2}(A_p')^2+\tfrac{1}{2}(A_s')^2+A_p'A_s'\cos(\Delta\omega t+\Delta\Phi') \quad (5)$$

wherein $\Delta\Phi'=\Phi_{P1}'-\Phi_{P2}'$, $A_p'$ and $A_s'$ are the amplitudes of the reflected and correlated $P_1$ and $P_2$ wave components, and $\Phi_{P1}'$ and $\Phi_{P2}'$ are the phase angles of the reflected $P_1$ and $P_2$ wave components. The output of the light detector 70 is processed by a band pass filter 80 having a center frequency equal to the beat frequency ($\Delta\omega$). The AC output of the band pass filter 80, which is provided to a phase-locking amplifier 90, is represented by the following Equation (6):

$$I_{sig}(\Delta\omega t)=A_p'A_s'\cos(\Delta\omega t+\Delta\Phi') \quad (6)$$

On the other hand, the reference light beam from the polarized beam splitter 51, which contains the reflected $S_1$ and $S_2$ wave components, is received by a light detector 71 to result in an optical heterodyne reference signal having a beat frequency ($\Delta\omega$) equal to $\omega_p-\omega_s$. The optical heterodyne reference signal can be represented by the following Equation (7):

$$I_{ref}(\Delta\omega t)=\frac{1}{2}A_p^2+\frac{1}{2}A_s^2+A_pA_s\cos(\Delta\omega t+\Delta\Phi) \quad (7)$$

wherein $\Delta\Phi=\Phi_{S1}-\Phi_{S2}=0$, $A_p$ and $A_s$ are the amplitudes of the reflected and correlated $S_1$ and $S_2$ wave components, and $\Phi_{S1}$ and $\Phi_{S2}$ are the phase angles of the reflected $S_1$ and $S_2$ wave components. $(A_p, A_s)$ and $(\Phi_{S1}, \Phi_{S2})$ are irrelevant to the surface plasma waves at the interface of the metal film and the test object. The output of the light detector 71 is processed by a band pass filter 81 having a center frequency equal to the beat frequency ($\Delta\omega$). The AC output of the band pass filter 81, which is also provided to the phase-locking amplifier 90, is represented by the following Equation (8):

$$I_{ref}(\Delta\omega t)=A_pA_s\cos(\Delta\omega t) \quad (8)$$

With reference to the optical heterodyne reference signal, the phase-locking amplifier 90 will detect and amplify the optical heterodyne test signal, thereby enhancing both sensitivity and signal-to-noise ratio. The output of the phase-locking amplifier 90 is received by a computer 91 for real-time detection of the amplitude $(A_p'A_p')$ of the optical heterodyne test signal and the time-varying change in the phase $(\Delta\Phi')$ of the optical heterodyne test signal, thereby enabling real-time detection of interaction between chemicals or bio-molecules and the biosensor.

Figure 14:
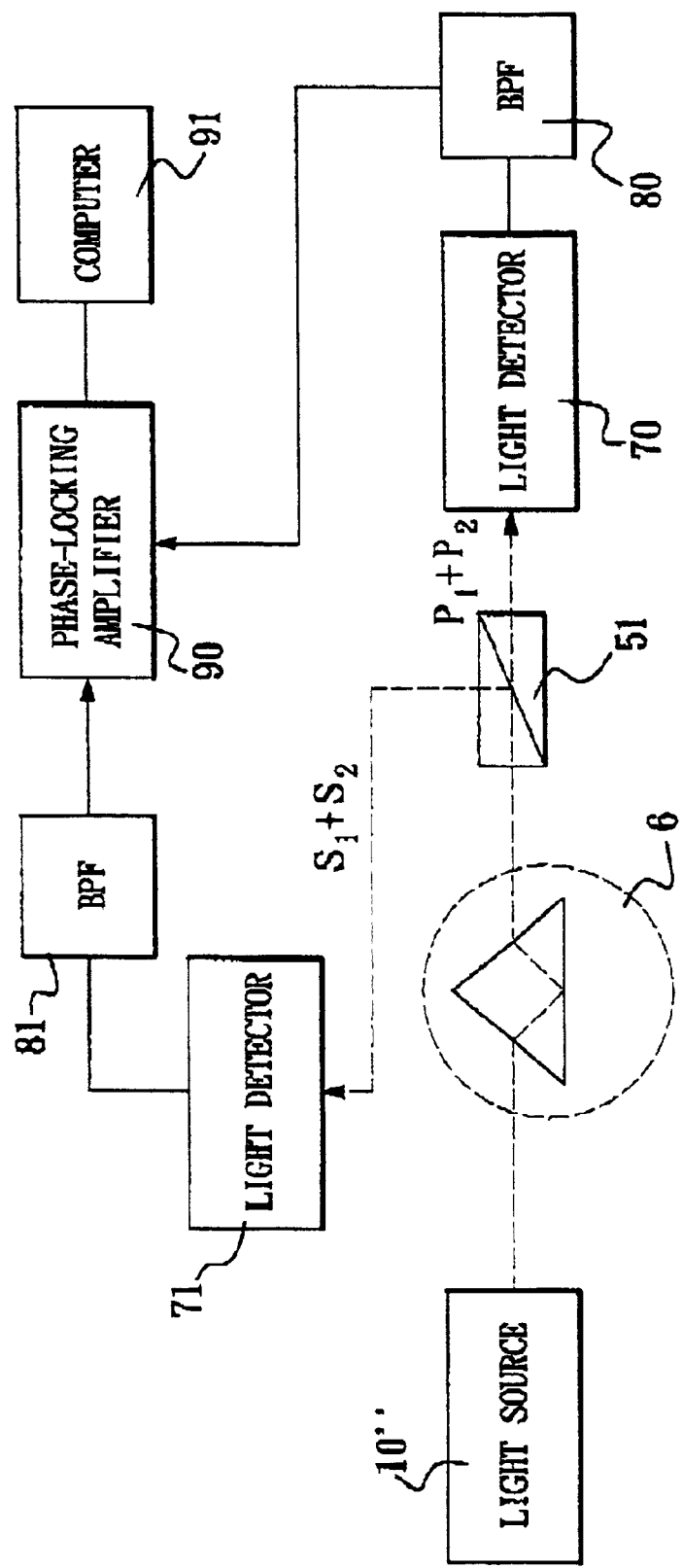
FIG. 14 is a schematic diagram illustrating the fourth preferred embodiment of an optical heterodyne surface plasma wave detecting apparatus according to the present invention.

FIG. 14 illustrates the fourth preferred embodiment of an optical heterodyne surface plasma wave detecting apparatus according to this invention. Unlike the embodiment of FIG. 13, the light source 10" is a stabilized two-frequency laser light source for generating two-frequency mutually orthogonal circular polarized light, i.e. L-wave and R-wave light, incident upon the total reflective component 6.

Figure 15:
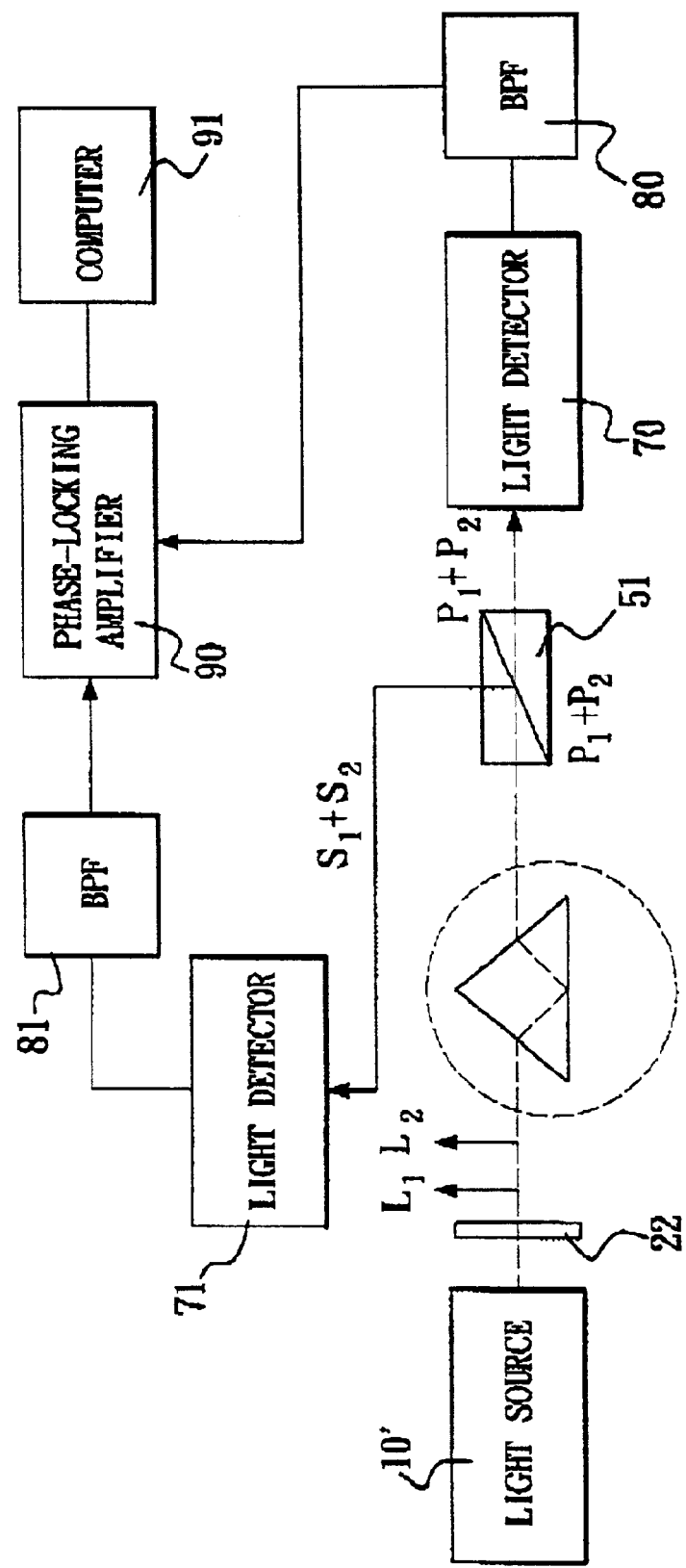
FIG. 15 is a schematic diagram illustrating the fifth preferred embodiment of an optical heterodyne surface plasma wave detecting apparatus according to the present invention.

FIG. 15 illustrates the fifth preferred embodiment of an optical heterodyne surface plasma wave detecting apparatus according to this invention. Unlike the embodiment of FIG. 13, the light source 10' is a stabilized two-frequency laser light source for generating two-frequency mutually orthogonal linear polarized light, Light from the light source 10' passes through an analyzer 22 to result in correlated linear polarized light $L_1$, $L_2$ having polarization directions parallel to the analyzer 22. The linear polarized light $L_1$, $L_2$ is directed to the total reflective component 6. The correlated $P_1$ wave and $P_2$ wave components of the linear polarized light $L_1$, $L_2$ are used to generate two surface plasma waves in the manner described beforehand and are reflected to result in the optical heterodyne test signal. The correlated $S_1$ and $S_2$ wave components of the linear polarized light $L_1$, $L_2$ are separated by a polarized beam splitter 51 from the reflected $P_1$ wave and $P_2$ wave components to result in the optical heterodyne reference signal.

Figure 16:
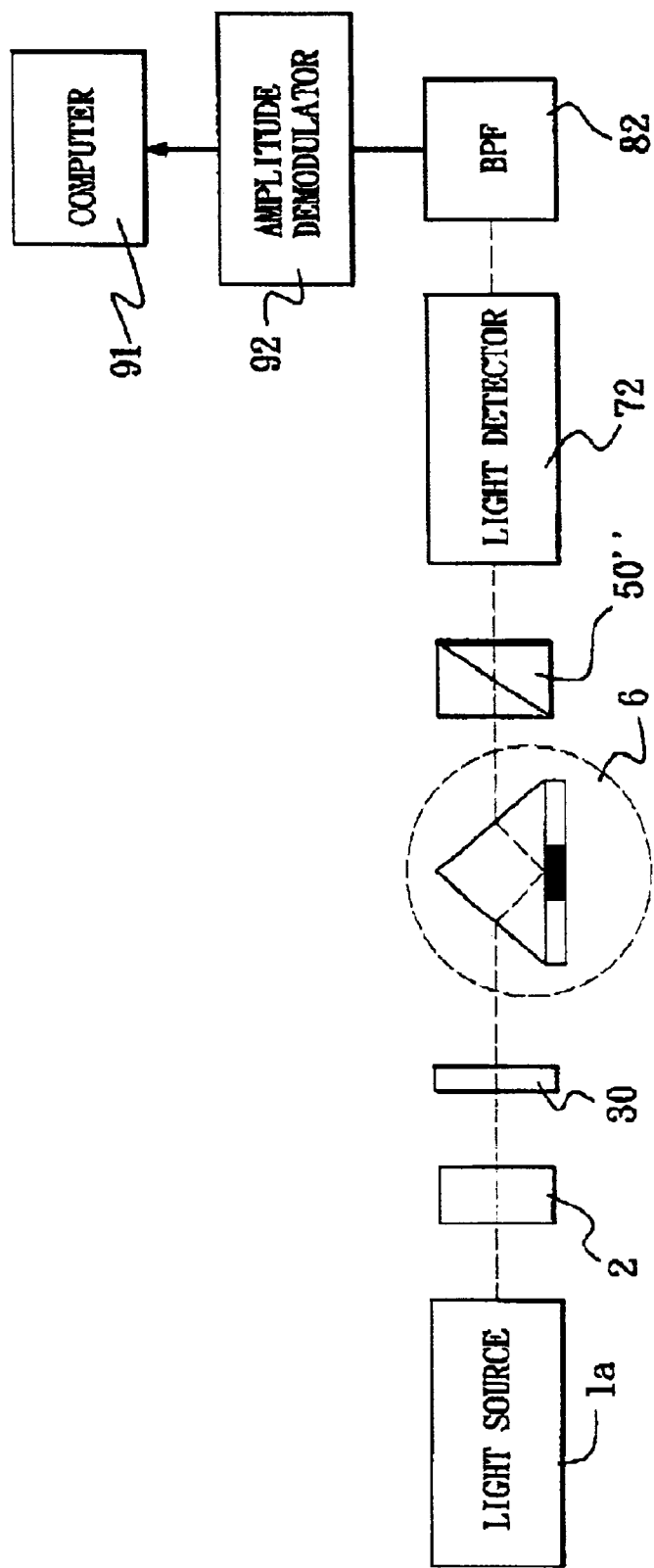
FIG. 16 is a schematic diagram illustrating the sixth preferred embodiment of an optical heterodyne surface plasma wave detecting apparatus according to the present invention.

FIG. 16 illustrates the sixth preferred embodiment of an optical heterodyne surface plasma wave detecting apparatus according to this invention. Unlike the embodiment of FIG. 12, light source (1a) is a two-frequency orthogonal circular polarized laser light source for generating R-wave and L-wave light that pass through a polarizer 2 and a cylindrical lens 30 before being directed to a total reflective component 6. A polarized beam splitter 50" separates correlated $P_1$ and $P_2$ wave components from light that was reflected from the total reflective component 6, and provides the same to a one-dimensional detector array 72, such as a one-dimensional CCD. The output of the detector array 72 is processed in sequence by a band pass filter 82 and an amplitude demodulator 92. A computer 91 receives the output of the amplitude demodulator 92 to achieve a multi-channel detecting function.

The following are some of the advantages of the optical heterodyne surface plasma wave detecting method and apparatus according to this invention:

1. The apparatus has a relatively simple construction.
2. The sensitivity is high, and a relatively wide linear range can be realized in the present invention because it relies on an amplitude sensitive method of an optical heterodyne test signal induced by two surface plasma waves, and not on the signal intensity response nor the shift in the resonance angle induced by one surface plasma wave.
3. The present invention combines optical heterodyne and phase-locking amplification techniques to enhance the signal-to-noise ratio.
4. Because the ratio of the amplitude of the optical heterodyne test signal to that of the optical heterodyne reference signal can be measured in the present invention, the adverse effect of unstable laser light intensity can be reduced to further enhance the sensitivity.
5. Fluorescent markers are not required so that the detection process is faster and simpler and that real-time detection of physical properties under test is permitted so as to be suitable for real-time measurement of changes in molecular interactions.
6. The present invention can be further extended to a multi-channel optical heterodyne surface plasma wave detecting system.

While the present invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

We claim:

1. An optical heterodyne surface plasma wave detecting method for measuring changes in dielectric coefficient or refractive index attributed to a test object on a total reflective component, the total reflective component having an interface with the test object, the detecting method comprising the steps of:
   a) processing a coherent light beam from a two-frequency orthogonal polarized coherent light source to form a reference light beam and a signal light beam, each of the reference light beam and the signal light beam having correlated $P_1$ and $P_2$ components, the correlated $P_1$ and $P_2$ components having two different frequencies and parallel polarization directions;
   b) directing the signal light beam to the total reflective component such that two surface plasma waves are generated at the interface;
   c) detecting the reference light beam and light which is reflected from the total reflective component so as to obtain an optical heterodyne reference signal and an optical heterodyne test signal, respectively; and
   d) comparing the optical heterodyne test signal with the optical heterodyne reference signal to determine changes in at least one of amplitude and phase of the optical heterodyne test signal relative to the optical heterodyne reference signal.

2. The optical heterodyne surface plasma wave detecting method as claimed in claim 1, wherein in step b), the incident angle of the signal light beam is adjusted so that the two surface plasma waves can be generated at the interface of the metal film and the test object.

3. The optical heterodyne surface plasma wave detecting method as claimed in claim 1, wherein, prior to step d), the optical heterodyne test signal and the optical heterodyne reference signal are processed by a respective band pass filter.

4. An optical heterodyne surface plasma wave detecting method for measuring changes in dielectric coefficient or refractive index attributed to a test object on a total reflective component, the total reflective component having an interface with the test object, the detecting method comprising the steps of:

a) directing a coherent light beam from a two-frequency orthogonal polarized coherent light source to the total reflective component such that two surface plasma waves are generated at the interface, the coherent light beam including a P-wave signal light beam (TM wave) and an S-wave reference light beam (TE wave), the P-wave signal light beam having correlated $P_1$ and $P_2$ components, the $P_1$ and $P_2$ components having two different frequencies and parallel polarization directions, the S-wave signal light beam having correlated $S_1$ and $S_2$ components, the $S_1$ and $S_2$ components having two different frequencies that are the same as those of the $P_1$ and $P_2$ components, respectively, the $S_1$ and $S_2$ components having parallel polarization directions that are orthogonal to those of the $P_1$ and $P_2$ components;

b) splitting light reflected from the total reflective component into the reference light beam and the signal light beam via a polarized beam splitter;

c) detecting the reference light beam and the signal light beam so as to obtain an optical heterodyne reference signal and an optical heterodyne test signal, respectively; and d) comparing the optical heterodyne test signal with the optical heterodyne reference signal to determine changes in at least one of amplitude and phase of the optical heterodyne test signal relative to the optical heterodyne reference signal.

5. The optical heterodyne surface plasma wave detecting method as claimed in claim 4, wherein in step a), the incident angle of the coherent light beam is adjusted so that the two surface plasma waves can be generated at the interface of the metal film and the test object.

6. The optical heterodyne surface plasma wave detecting method as claimed in claim 4, wherein, prior to step d), the optical heterodyne test signal and the optical heterodyne reference signal are processed by a respective band pass filter.

7. An optical heterodyne surface plasma wave detecting apparatus for measuring changes in dielectric coefficient or refractive index attributed to a test object, comprising:

a two-frequency orthogonal polarized coherent light source for generating a reference light beam and a signal light beam, each of which has two correlated wave components, the wave components having two different frequencies and parallel polarization directions;

a total reflective component having an interface with the test object, the signal light beam being directed to the total reflective component such that two surface plasma waves are generated at the interface;

a first light detector for detecting the reference light beam so as to obtain an optical heterodyne reference signal;

a second light detector for detecting light reflected from the total reflective component so as to obtain an optical heterodyne test signal; and a signal processor, coupled to the first and second light detectors, for comparing the optical heterodyne test signal with the optical heterodyne reference signal to determine changes in at least one of amplitude and phase of the optical heterodyne test signal relative to the optical heterodyne reference signal.

8. The optical heterodyne surface plasma wave detecting apparatus as claimed in claim 7, wherein the wave components of each of the reference and signal light beams are correlated $P_1$ and $P_2$ wave components (TM wave), each of the optical heterodyne test signal and the optical heterodyne reference signal having a beat frequency equal to the difference between the frequencies of the correlated $P_1$ and $P_2$ wave components.

9. The optical heterodyne surface plasma wave detecting apparatus claimed in claim 7, further comprising first and second band pass filters, each of which connects a respective one of the first and second light detectors to the signal processor and processes a respective one of the optical heterodyne reference signal and the optical heterodyne test signal.

10. The optical heterodyne surface plasma wave detecting apparatus as claimed in claim 7, wherein the signal processor includes a phase-locking amplifier.

11. An optical heterodyne surface plasma wave detecting apparatus for measuring changes in dielectric coefficient or refractive index attributed to a test object, comprising:

a two-frequency orthogonal polarized coherent light source for generating a P-wave signal light beam and an S-wave reference light beam, the P-wave signal light beam having correlated $P_1$ and $P_2$ components (TM wave), the $P_1$ and $P_2$ components having two different frequencies and parallel polarization directions, the S-wave signal light beam having correlated $S_1$ and $S_2$ components (TE wave), the $S_1$ and $S_2$ components having two different frequencies that are the same as those of the $P_1$ and $P_2$ components, respectively, the $S_1$ and $S_2$ components having parallel polarization directions that are orthogonal to those of the $P_1$ and $P_2$ components;

a total reflective component having an interface with the test object, light from the coherent light source being directed to the total reflective component such that two surface plasma waves are generated at the interface;

a polarized beam splitter for splitting light reflected from the total reflective component into the reference light beam and the signal light beam;

a first light detector for detecting the reference light beam so as to obtain an optical heterodyne reference signal;

a second light detector for detecting the signal light beam so as to obtain an optical heterodyne test signal; and a signal processor, coupled to the first and second light detectors, for comparing the optical heterodyne test signal with the optical heterodyne reference signal to determine changes in at least one of amplitude and phase of the optical heterodyne test signal relative to the optical heterodyne reference signal.

12. The optical heterodyne surface plasma wave detecting apparatus as claimed in claim 11, further comprising first and second band pass filters, each of which connects a respective one of the first and second light detectors to the signal processor and processes a respective one of the optical heterodyne reference signal and the optical heterodyne test signal.

13. The optical heterodyne surface plasma wave detecting apparatus as claimed in claim 11, wherein the signal processor includes a phase-locking amplifier.

14. An optical heterodyne surface plasma wave detecting method for measuring changes in dielectric coefficient or refractive index attributed to a test object on a total reflective component, the total reflective component having an interface with the test object, the detecting method comprising the steps of:

a) generating a signal light beam having correlated $P_1$ and $P_2$ components (TM wave), the correlated $P_1$ and $P_2$ components having two different frequencies and parallel polarization directions;

b) directing the signal light beam to the total reflective component such that two surface plasma waves are generated at the interface;

c) detecting light which is reflected from the total reflective component so as to obtain an optical heterodyne test signal; and d) determining a time-varying change in amplitude of the optical heterodyne test signal.

15. An optical heterodyne surface plasma wave detecting apparatus for measuring changes in dielectric coefficient or refractive index attributed to a test object, comprising:

a two-frequency coherent light source for generating a signal light beam having correlated $P_1$ and $P_2$ components (TM wave), the correlated $P_1$ and $P_2$ components having two different frequencies and parallel polarization directions;

a total reflective component having an interface with the test object, the signal light beam being directed to the total reflective component such that two surface plasma waves are generated at the interface;

a light detector for detecting light reflected from the total reflective component so as to obtain an optical heterodyne test signal; and a signal processor, coupled to the light detector, for determining a time-varying change in amplitude of the optical heterodyne test signal.

16. The optical heterodyne surface plasma wave detecting apparatus as claimed in claim 15, wherein the signal processor includes an amplitude demodulator.

* * * * *